United States Patent [19]
Bootman et al.

[11] Patent Number: 4,543,088
[45] Date of Patent: Sep. 24, 1985

[54] SELF-SEALING SUBCUTANEOUS INJECTION SITE

[75] Inventors: Matthew W. Bootman, Bakersfield; Ronald K. Yamamoto, Goleta, both of Calif.

[73] Assignee: American Hospital Supply Corporation, Evanston, Ill.

[21] Appl. No.: 549,092

[22] Filed: Nov. 7, 1983

[51] Int. Cl.⁴ ............................................. A61M 25/00
[52] U.S. Cl. ...................................... 604/93; 604/175
[58] Field of Search ............................. 604/175, 8–10, 604/212, 93

[56] References Cited

U.S. PATENT DOCUMENTS 3,831,583  8/1974  Edmunds, Jr. et al. ............. 128/346
4,364,395 12/1982  Redmond et al. ..................... 604/10
4,400,169  8/1983  Stephen ......................... 604/175 X
4,405,305  9/1983  Stephen et al. ................... 604/29 X Primary Examiner—Stephen C. Pellegrino
Attorney, Agent, or Firm—Roger A. Williams

[57] ABSTRACT

A self-sealing subcutaneous injection site for implantation in the body includes a housing having a bottom wall and a generally resilient dome-shaped wall which defines an interior chamber within the housing. The interior chamber has a durometer and shape for providing compressive forces within the dome-shaped wall for sealing punctures extending through the dome-shaped wall upon fluid pressurization of the interior chamber. A conduit extends through the dome-shaped wall into the interior chamber to provide a fluid-flow passageway to the chamber.

11 Claims, 7 Drawing Figures

4,543,088

SELF-SEALING SUBCUTANEOUS INJECTION SITE

BACKGROUND OF THE INVENTION

The invention herein is directed to a self-sealing subcutaneous injection site. The injection site provides a resealable puncture housing for surgical implantation.

Implantable injection sites are used in patient treatment techniques wherein it is desirable or necessary to administer or withdraw a fluid to a site within a patient. Subcutaneous injection sites can be used in combination with skin expanders or inflatable mammary prostheses. The use of a subcutaneous injection site with such skin expanders and prostheses provides a means for introducing additional inflationary fluid to either the skin expander or mammary prosthesis which can be interconnected to the subcutaneous injection site. The use of a subcutaneous injection site for such medical devices provides an ambulatory condition to the patient as the patient can continue about their normal function and call upon the physician only at the time additional fluid needs to be administered or withdrawn. The use of a subcutaneous injection site in association with a skin expansion chamber is described in U.S. Pat. No. 4,217,889 to Radovan.

The subcutaneous injection site can also be used for the administration of medication to a patient. For example, in many therapeutic procedures there is a need to implant a drug delivery device. Such an implantable drug delivery device provides a bolus or therapeutic dose of the drug contained therein to a particular location within the patient's body. In order to replenish the drug in the implanted device, a self-sealing subcutaneous injection site can be provided in fluid communication with the drug delivery device. In some instances, a self-sealing subcutaneous injection site can itself be the drug delivery device. The self-sealing subcutaneous injection site provides a means for administering additional medicament into the device as the medicament can be injected using a syringe inserted subcutaneously into the injection site without the need for a subsequent surgical procedure.

Resealable puncture housing for surgical implantation are disclosed in U.S. Pat. No. 3,310,051; U.S. Pat. No. 3,831,583; and U.S. Pat. 4,190,040. U.S. Pat. No. 3,310,051 describes a silicone capsule for implantation beneath the skin into which fluid can be injected or withdrawn by hypodermic syringe. The puncturable capsule described therein works well when connected to a ventricular catheter for removing or injecting fluid into a patient's brain. However, if a high pressure is experienced by the fluid within the capsule, then the housing for such capsule can leak at the needle puncture sites, thereby causing the fluid within the capsule to flow into the surrounding tissue.

U.S. Pat. No. 3,831,583 describes a plug-shaped capsule that contains a silicone gel for resealing needle punctures of the surgically implanted capsule. The shape and dimension of the plug-like sealant chamber on such an implantable housing is not conveniently usable with the injection angle commonly used for nurses and physicians. In many instances, it is difficult to palpate and locate the particular plug-like chamber. To gain control over subcutaneous injections, the hypodermic needle is frequently placed at a widely angled position almost parallel to the skin. This gives the operator better control of the injection point and puncture depth than a position more perpendicular to the skin. Thus, the device of U.S. Pat. 3,831,583 is not ideally suitable for use.

The implantable resealable puncture housing disclosed in U.S. Pat. No. 4,190,040 was an improvement over the previous implantable resealable puncture housings. The housing in this patent utilizes a laminated structure wherein a silicone gel is sandwiched between two silicone layers. Such a device did provide for a more varied angle of penetration for a hypodermic needle being inserted into the chamber. However, the housing is not ideally structured for repeated puncturing with hypodermic needles as if a large number of punctures are desired, gel bleed from the housing can occur. In such instances, it is undesirable to have silicone gel flow into the surrounding tissue. In addition, such a device after repeated puncturing does not provide for effective sealing, particularly when the fluid in the chamber within the housing is under elevated pressures such as pressures at or near the blood pressure levels of a patient.

It would be desirable to provide a self-sealing subcutaneous injection site which can be used in situations requiring repeated and periodic puncturing while maintaining a self-sealing capability even under elevated pressures within the chamber of the injection site.

SUMMARY OF THE INVENTION

The present invention overcomes the problems described above and provides a self-sealing subcutaneous injection housing having a bottom wall and a generally dome-shaped resilient wall which defines an interior chamber within the housing. The dome-shaped wall of the housing has a durometer and shape for providing compressive forces within the wall for sealing punctures through the wall upon fluid pressurization within the chamber. A conduit extends through the wall and interconnects with the chamber for providing fluid flow into and out of the chamber. The conduit can provide for interconnecting with a catheter or other suitable tubing.

More particularly, the self-sealing subcutaneous injection site herein includes a housing having a bottom wall, which bottom wall can be of a material that is impenetrable by the cannula of a hypodermic syringe. Such a bottom wall prevents the insertion of a hypodermic syringe completely through the injection site while introducing fluid to the injection site. The housing further includes a generally dome-shaped resilient wall defining an interior chamber. The interior chamber has a convex upper wall formed by a portion of the dome-shaped wall of the housing. In addition to the upper wall of the chamber being convex, the sidewall of the chamber can be convex and formed by a portion of the dome-shaped wall of the housing. The convex shape of the upper wall and sidewall of the chamber provides compressive forces within the upper wall or sidewall for sealing punctures through either the upper wall or sidewall upon fluid pressurization within the chamber.

DETAILED DESCRIPTION

Figure 1:
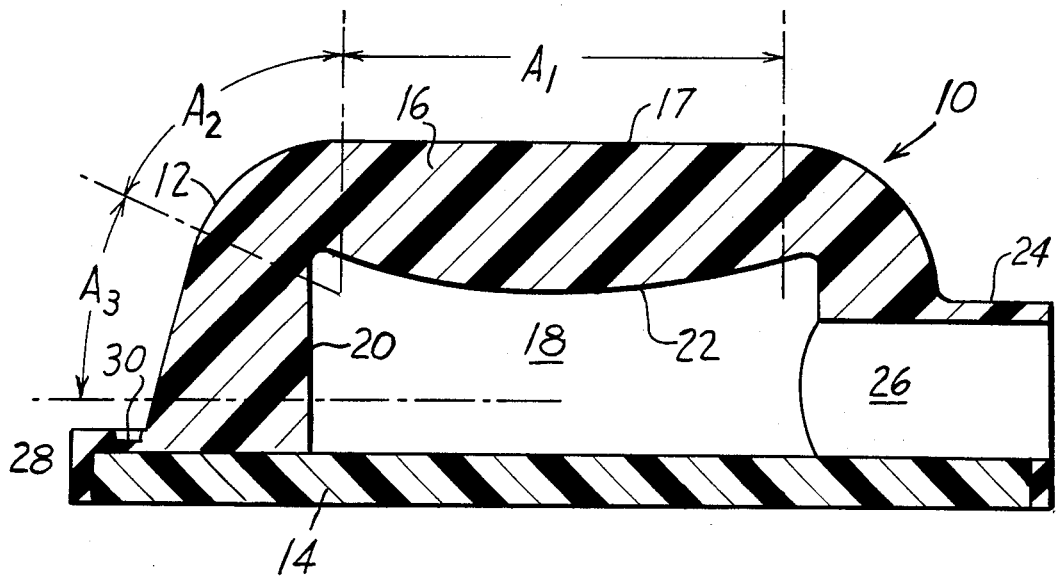
FIG. 1 is a cross-sectional side elevational view of a self-sealing subcutaneous injection site.

The self-sealing subcutaneous injection site will be described with regard to the accompanying drawings. In particular, FIG. 1 shows an embodiment of a self-sealing subcutaneous injection site 10. For facilitating description herein, the injection site will be referred to as the injection site. The injection site 10 has a housing 12 which consists of an elastomeric material which is biocompatible with the human physiognomy. An acceptable material from which the housing can be constructed is silicone elastomer. The housing includes a generally dome-shaped wall 16 and a bottom wall 14. The bottom wall can be constructed of a resilient material such as silicone elastomer or can be constucted of a material which is impenetrable to puncture by a needle cannula such as a polyethylene, polycarbonate and the like. When the bottom wall 14 is constructed of such an impenetrable material, it functions as a needle guard preventing a needle cannula, which is inserted into the housing to fill the chamber therein, from completely penetrating through the injection site. The bottom wall and dome-shaped wall are sealed together.

The dome-shaped wall of the housing defines an inner chamber 18 having a volume for receiving fluid to be introduced or withdrawn from a patient's body following implantation of the injection site. The volume of the chamber can vary depending upon the contemplated end use for the injection site. With regard to FIGS. 1 and 3-6, the embodiment of the injection site shown therein has an inner chamber 18 formed by chamber sidewall 20 and chamber upper wall 22. Both the chamber sidewall 20 and chamber upper wall 22 are formed by at least a portion of the dome-shaped wall 16 of the housing. In the embodiment shown therein, the chamber sidewall 20 is generally a straight, vertically extending sidewall. As can be seen from the top view shown in FIG. 6, the chamber sidewall 20 extends in a circle, forming a generally cylindrical chamber 18. The chamber 18 can have geometric configurations other than cylindrical.

The chamber upper wall 22 has a generally convex shape with the upper wall convex in regard to the chamber 18. The outer surface of the dome-shaped wall 16, at least at the upper surface generally designated as area $A_1$ in FIG. 1, has a generally or substantially flat surface 17. The geometric shape of the dome-shaped wall in the area $A_1$, including the convex surface and chamber upper wall 22, combine with the durometer of the resilient material to provide compressive forces within the dome-shaped wall such that such forces can close a puncture extending through the dome-shaped wall. The self-sealing capability of the injection site herein is illustrated in FIGS. 5 and 6.

Figure 5:
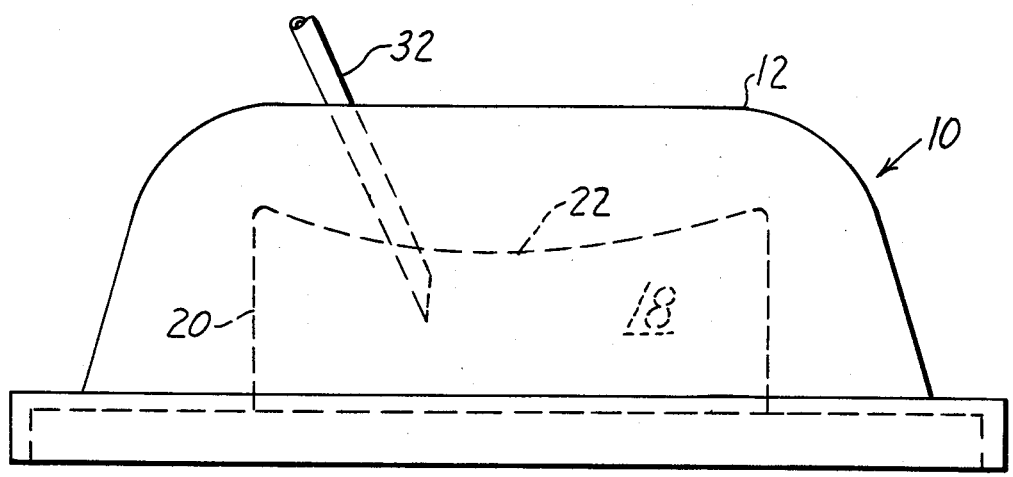
FIG. 5 is a side elevational view of the embodiment of the self-sealing injection site shown in FIG. 1 and showing penetration by a needle cannula.
Figure 6:
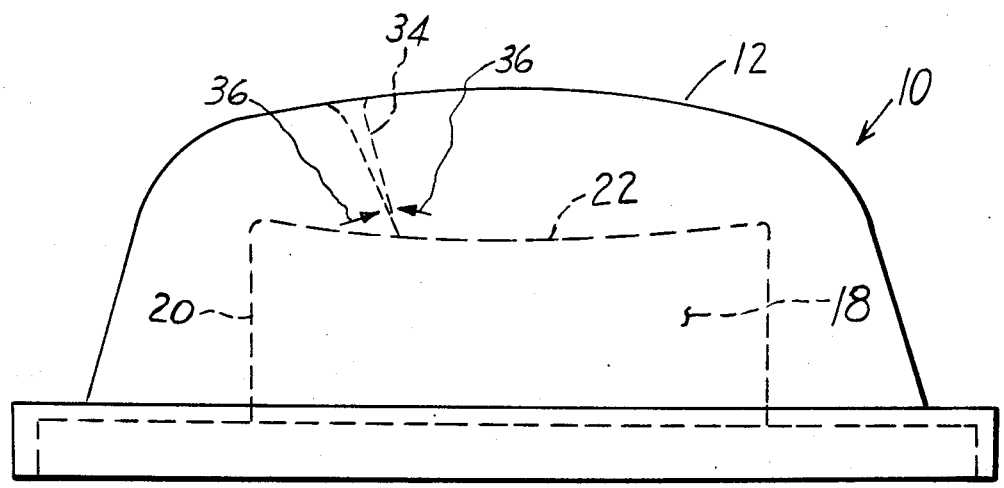
FIG. 6 is a side elevational view of the embodiment shown in FIG. 5 with the needle cannula withdrawn.

With regard to FIG. 5 and 6, the embodiment of the injection site shown in FIG. 1 is illustrated in a side elevational view. FIG. 5 shows the injection site being punctured with a needle cannula 32 which penetrates the dome-shaped wall 16 and extends into the inner chamber 18. A syringe (not shown) filled with a fluid to be introduced to the chamber can be connected to the needle cannula. As the dome-shaped wall is constructed of a resilient material, it can be punctured by the needle cannula. Using the syringe, fluid is introduced to the inner chamber 18. As fluid is introduced to the chamber, the fluid creates a pressure within the chamber, which pressure is exerted against the walls of the inner chamber. The pressure exerted against the chamber upper wall 22 forces the upper wall outwardly. Upon withdrawal of the needle cannula 32, the puncture 34 is closed and effectively sealed against fluid flow by the elastomeric properties of the material comprising the done-shaped wall 16 and the compressive forces in the done-shaped wall as a result of its structure. Such compressive forces are shown by the vectors 36 which arise as a result of the fluid pressure exerted against the convex chamber upper wall 22 which causes the chamber upper wall to lose its convexity and thereby exert a closing pressure against the puncture 34 effectively sealing the puncture at especially its innermost portion near the chamber upper wall 22. That is, as the chamber is pressurized by the fluid the elastic dome-shaped wall is compressed. This compression is greatest at the inside surface such as the chamber upper wall 22. The compression and resulting material deformation causes the puncture to be effectively sealed along the chamber upper wall 22.

The embodiment shown in FIGS. 1 and 3-6 can be used in situations where there is a strong likelihood that the chamber will be filled by penetrating the dome-shaped wall of the injection site in the area designated as a $A_1$ on FIG. 1. Such an embodiment provides an injection site which can be repeatedly punctured by a needle cannula while introducing fluid into the inner chamber, but which retains such fluid and greatly inhibits leaking of such fluid into the surrounding tissue. In addition, such a device can be used for infusing fluids into pressurized areas which may be experienced in the body such as in the circulatory system.

Figure 7:
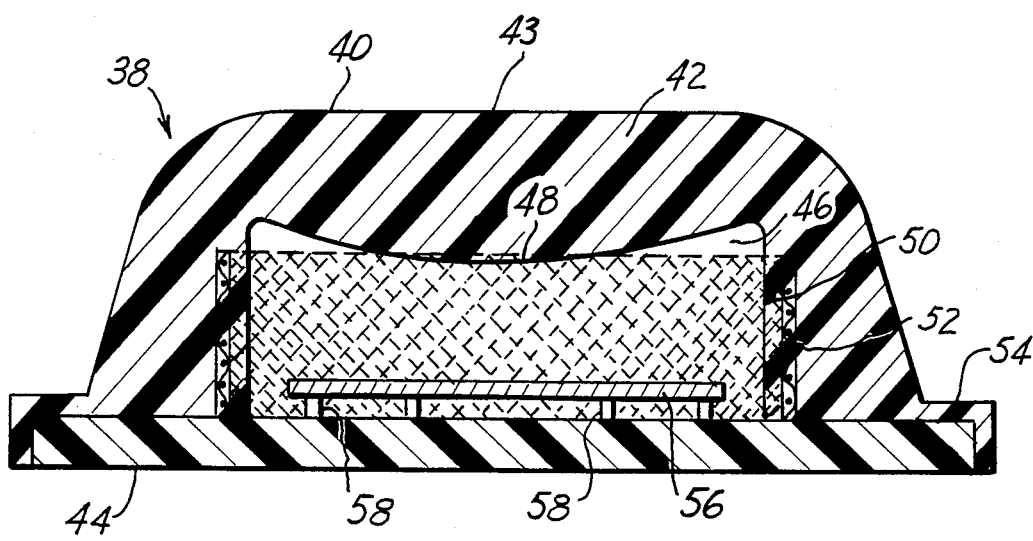
FIG. 7 is a side cross-sectional elevational view of still another embodiment of a self-sealing subcutaneous injection site.

In some instances, it is desirable to provide an injection site which can be punctured with a needle cannula in areas other than along the upper surface. For example, the embodiment shown in FIGS. 1 and 3-6 has a generally vertically extending chamber sidewall 20. The sidewall and the corresponding area are designated as $A_3$ in FIG. 1 along with the upper corner between the chamber sidewall and chamber upper wall in the area generally designated as $A_2$. During filling of the chamber 18 and pressurization of the chamber, the chamber sidewall 20 and corner area experience a tensioning and resulting wall strain. The material deformation through such tensioning causes any puncture extending the corresponding areas $A_2$ and $A_3$ to open along the inside surface which may take the shape of a concave surface at such areas. Upon such an occurrence, the surface adhesion of the elastomer along the puncture is easily overcome and leakage of the fluid from the chamber can occur through such puncture. The surfaces of the edge radius between the chamber upper wall and chamber sidewall and the chamber sidewall surface in the tangential (or horizontal) direction can be tensioned upon achieving high pressures within the chamber. The edge radius region can go into tension because of circumferential stresses and due to its concave surface. The chamber sidewall surface can go into tension tangentially because of the circumferential stress upon pressurization. These undesirable edge and chamber sidewall deformations can be lessened by constructing the embodiment shown in FIG. 2 or by providing a cuff of reinforcing material such as Dacron, Nylon and the like extending around and imbedded in the chamber sidewall as is shown in FIG. 7. The high modulus Dacron material prevents significant hoop strain at pressures which can be realized in the chamber.

With regard to FIG. 7, another embodiment of the self-sealing subcutaneous injection site is illustrated. In the embodiment shown in FIG. 7, the injection site has the structure substantially equivalent to that of the embodiment shown in FIG. 1. Injection site 38 of FIG. 7 includes a housing 40 having a resilient dome-shaped wall 42. The upper outer surface 43 of the dome-shaped wall is generally flat. The housing includes a bottom wall 44 which can be sealed to the dome-shaped wall to form with the dome-shaped wall and interior chamber 46. The interior 46 has a convex chamber upper wall 48 and a chamber sidewall 50. Imbedded within the chamber sidewall is a reinforcing material such as a reinforcing mesh which can be constructed of Dacron, Nylon and the like. The reinforcing cuff 52 substantially prevents distortion of the sidewall, thereby assisting the sidewall in closing or sealing any punctures which extend therethrough. That is, the reinforcing cuff prevents distortion of the sidewall due to increased pressures which can occur in the inner chamber 46. The injection site 38 also can include an outwardly extending flange 54. Also in the embodiment shown in FIG. 7, the injection site therein includes a separate needle guard 56 which is constructed of a material impermeable to puncture by a needle cannula. the needle guard 56 is positioned along the bottom wall 44 within the interior chamber 46. The needle guard can be supported and spaced from the bottom wall by legs 58.

Figure 2:
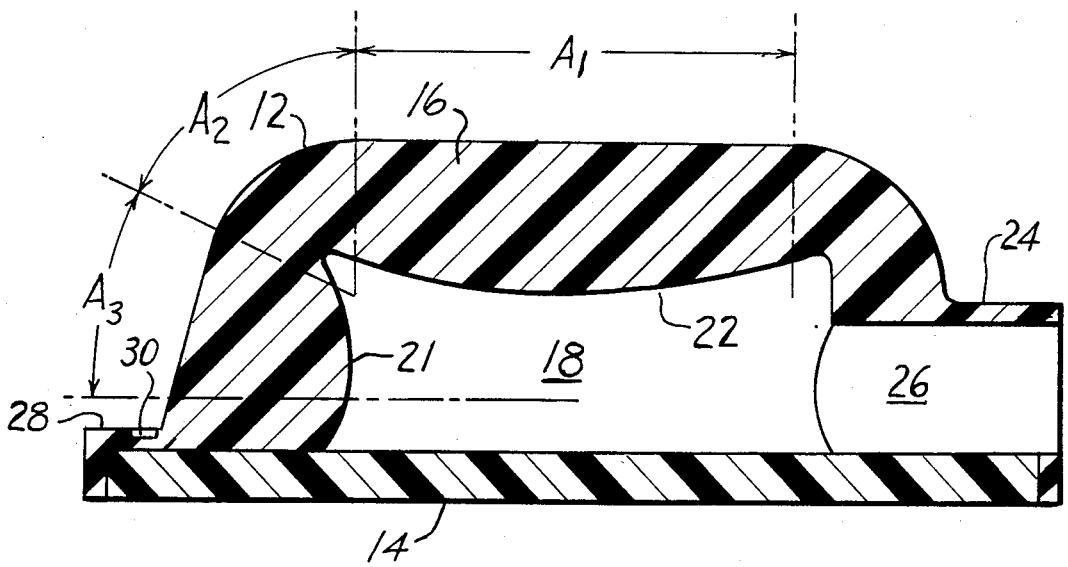
FIG. 2 is a cross-sectional side elevational view of another embodiment of a self-sealing subcutaneous injection site.
Figure 3:
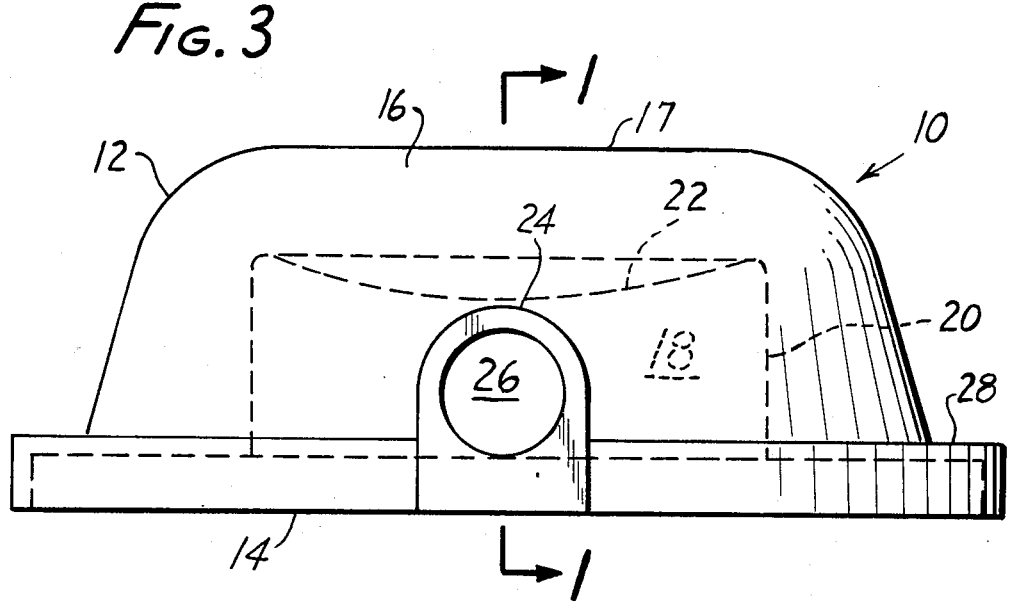
FIG. 3 is a side elevational view of the embodiment of the self-sealing subcutaneous injection site shown in FIG. 1.

In the embodiment shown in FIG. 2, elements that are the same as the elements of the embodiment shown in FIG. 1 are shown using the same numbers. The embodiment shown in FIG. 2 is identical to that of FIG. 1 with the exception that the chamber sidewall 21 has a convex configuration as opposed to the generally straight-walled chamber sidewall 20 of the embodiment in FIG. 1. Such a convex structure along the chamber sidewall performs in much the same manner as above described with regard to the convex chamber upper wall 22 in the first embodiment. That is, the embodiment shown in FIG. 2 can be repeatedly punctured either through the area shown as $A_1$ or $A_3$ in FIG. 2 and maintain its self-sealing capability. The only area remaining on the injection site wherein the greatest beneficial properties of the chamber wall structures is not realized is in the area designated as $A_2$. The likelihood of puncturing such a small area with a needle cannula is reduced in view of the much greater areas in the areas designated $A_1$ and $A_3$.

The embodiment shown in FIG. 2 as well as that in FIG. 1 can be used for implanting in high pressure situations such as accessing arterial blood or as an injection site for inflating skin expansion bladders. The embodiment shown in FIG. 2 can provide for widely angled puncture positions for a syringe needle cannula used to introduce fluid into the inner chamber 18.

Again with regard to both embodiments shown in the accompanying drawings, the housing includes a conduit 24 which can be a cylindrical conduit integrally formed with the dome-shaped wall 16. The conduit 24 provides a fluid-flow passageway 26 for providing fluid flow to and from the chamber. The fluid-flow passageway 26 can receive a tubing connector for connecting the injection site to a catheter or other tubing so that fluid introduced to the inner chamber can be delivered through such tubing to a site within the patient.

Figure 4:
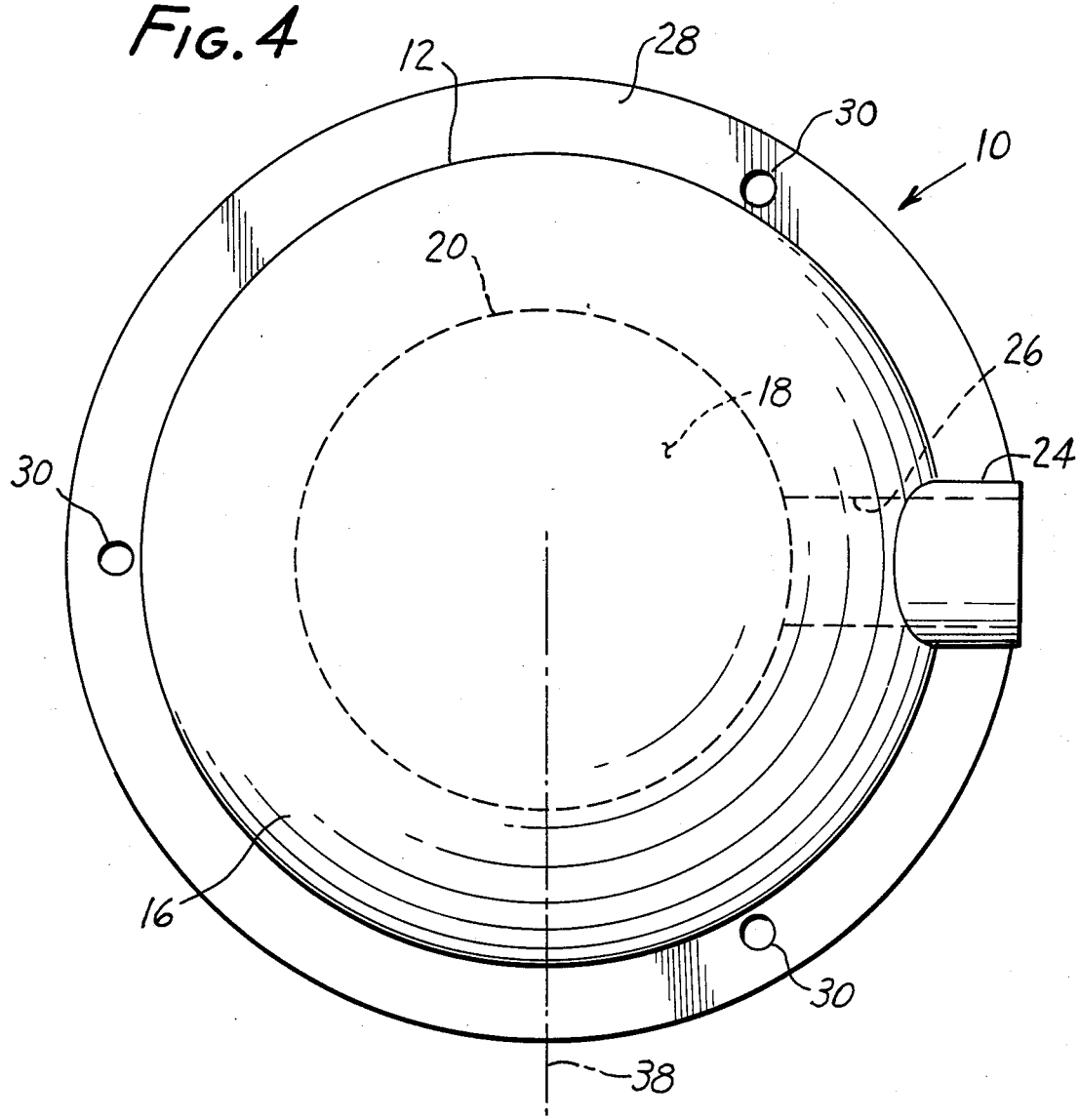
FIG. 4 is a top elevational view of the self-sealing subcutaneous injection site embodiment shown in FIG. 1.

The housing can include an outwardly extending flange 28. The housing can also be constructed in any geometric configuration, but in the preferred embodiment a circular configuration as is shown in FIG. 4 is utilized. As can be seen in the drawings and especially in FIG. 4, the outwardly extending flange 28 extends around the periphery of the injection site. The flange can extend around only portions of the periphery of the injection site. One purpose of the flange is to provide for attachment of the injection site to a location within a patient. For example, the flange includes suture sites 30 through which sutures can be taken to fix the injection site subcutaneously within a patient. Other techniques for fixing the injection site within the patient can be used such as using surgical staples. The suture sites 30 can be apertures opening through the outwardly extending flange or can merely be areas along the flange of lesser thickness than the flange itself such that such suture sites can be easily penetrated by a surgical needle while suturing.

As state above, various geometric shapes can be employed in constructing the injection site herein as long as the inner chamber is constructed as described, namely providing the chamber wall most likely to be punctured with a convex structure. In the preferred embodiment, the injection site has the outer configuration with a rather flat upper surface 17 on the dome-shaped wall 16 as is shown in FIGS. 1 and 2. Such a configuration provides, upon fluid pressurization of the chamber, a direction of expansion for the convex chamber upper wall.

The size of the injection site can be modified according to the requirements for the treatment technique to which the injection site is being used. That is, the size can be varied to provide for palpation, different needle sizes, number of injections and expected back pressures in order to accomplish the desired resealing characteristics. In this manner, the injection site can be modified to meet the demands for placement into different body structures such as intrathecal, venous, arterial, intramuscular, and the like.

Integral rigid connectors can be incorporated into the injection site by fitting such connectors into the fluid passageway 26 to provide and simplify attachment of catheters and tubing. The injection site or portions thereof can be made radiopaque by incorporating materials having a radiopacity during molding or manufacture of the injection site. By using radiopaque materials, the position of the device can be verified post-operatively.

The utility and beneficial properties of an injection site made in conformity with the invention herein demonstrated in a series of tests wherein injection sites were repeatedly punctured. The tests were designed to determine the efficacy of injection sites and their ability to reseal after repeated needle puncture and for their use against transient pressures as high as 200 centimeters of water which is comparable to a high arterial blood pressure.

The test technique was performed using each injection site dome configuration by puncturing each injection site up to the indicated number of punctures with a needle cannula that was either 19 gauge or 21 gauge as indicated having a regular bevel. The punctures were randomly distributed over the area of the injection site with the indicated areas being those areas as shown and designated in FIGS. 1 and 2. The injection sites were also tested for fluid leak rate from the inner chamber at a pressure of 200 centimeters of water. The injection site chambers were pressurized to 200 centimeters water pressure and the amount of extruded fluid was determined by soaking up the beads of fluid with a tared piece of absorbent paper toweling which was subsequently weighed to determine the amount of fluid.

In the first series of tests, three injection sites were tested. The injection sites tested basically had the structure as shown in FIG. 1 with the following limitations. The injection site designated as "A" was substantially identical to the embodiment shown in FIG. 1; the injection site designated as "B" was substantially similar to the injection site shown in FIG. 1 with the exception that the chamber sidewall was concave; and the injection site identified as "C" was substantially the same in all material aspects as the injection site shown in FIG. 2. The injection sites were punctured in the following pattern of puncture distribution: 25 punctures in the top region generally designated area $A_1$ of FIG.1; 10 punctures in the edge region generally designated area $A_2$; and 200 punctures in the side region generally designated area $A_3$. For the punctures in the side region $A_3$, the area punctured included the one-half of the injection site opposite the fluid-flow passageway. That is, the one-half of the injection site as if a diameter were drawn separating the injection site along the line 38 as shown in FIG. 4. The following results shown in Table 1 were obtained with the pressure readings in centimeters of water:

TABLE I

| Injection Site | 25 Area $A_1$ | 10 Area $A_2$ | 50 Area $A_3$ | 100 Area $A_3$ | 50 Area $A_3$ |
|---|---|---|---|---|---|
| A | >1200 | 240 | 190 | 180 | 76 |
| A | >1200 | 320 | 325 | 270 | 128 |
| B | >1200 | 340 | 340 | 250 | 78 |
| B | >1200 | 240 | 180 | 140 | 56 |
| C | >1200 | 550 | 342 | 297 | 125 |
| C | >1200 | 440 | 320 | 245 | 138 |

From the above data it can be readily seen that the three injection site configurations provide injection sites which can be repeatedly punctured through area $A_1$ and maintain effective sealing even under high pressures in the chambers of the respective injection sites. The injection site C can be used when punctured repeatedly in area $A_3$ and maintain effective sealing.

When the above three configurations of injection sites were tested by pressurizing the chambers up to 200 centimeters of water pressure, the resultant leakage following the 235 punctures is as shown in the following table:

TABLE II

| Injection Site | Ml/Minute | Ml/Hour |
|---|---|---|
| A | 0.076 | 4.56 |
| A | 0.013 | 0.78 |
| B | 0.028 | 1.70 |
| B | 0.049 | 2.94 |
| C | 0.038 | 2.28 |
| C | 0.020 | 1.2 |

The average leak rate in milliliters per hour for the three injection sites were A, 2.60; B, 2.32; and C, 1.74.

The following tests using the above described techniques were also performed to determine leak pressures around and along various areas of an injection site having the structure shown in the embodiment in FIG. 2. Six different injection sites were tested. Punctures were made using either a 21 gauge or a 19 gauge hypodermic needle having a regular bevel. The goals of the tests on such six injection sites were to determine the internal pressure which would cause leakage of the hypodermic needle punctures in specific areas on the injection site dome. The domes were repeatedly punctured, and the resulting pressure required to form a fluid bead on the surface of each injection site in centimeters of water recorded for the number of punctures. In the first section of the following table, the injection site was randomly punctured with 25 punctures in the area $A_1$, 10 punctures in the area $A_2$, and values determined for 10, 25 and 100 punctures in the area $A_3$. The second portion of the table shows the results upon puncturing one quadrant of the injection site with 25 punctures in each of the areas $A_1$ and $A_2$. The third section of the table provides the results of minimum leak pressures determined for the injection site after all of the punctures were made. The leak pressures were recorded for leaks only in the areas recently punctured.

TABLE III

| | | I. All Quadrants | | | | | II. 1 Quadrant | | | | III. |
|---|---|---|---|---|---|---|---|---|---|---|---|
| | | Top $A_1$ | Edge $A_2$ | Side $A_3$ | | | Top $A_1$ | Edge $A_2$ | Top $A_1$ | Edge $A_2$ | Minimum Leak |
| Dome | Needle | 25 | 10 | 10 | 25 | 100 | 25 | 25 | 25 | 25 | Pressure |
| 1 | 21 g | N.L. | 328 | 460 | 390 | 256 | N.L. | 368 | 443 | 214 | 152 |
| 2 | 21 g | N.L. | 726 | 606 | 554 | 188 | 328 | 204 | 219 | 162 | 119 |
| 3 | 21 g | 770 | 698 | 476 | 387 | 242 | 642 | 256 | 495 | 238 | 176 |
| 4 | 21 g | 689 | 261 | 361 | 298 | 220 | 470 | 264 | 346 | 212 | 124 |
| 5 | 19 g | N.L. | 681 | 608 | 605 | 448 | 428 | 416 | 336 | 304 | 183 |
| 6 | 19 g | 983 | 943 | 950 | 708 | 422 | 406 | 378 | 346 | 312 | 168 |

(N.L. = No Leak ≧ 1400 cm $H_2O$)

As can be seen from the above table, the injection site structure performed very well with pressures requiring greater than 200 centimeters of water in order to form a bead on the surface of the injection site and 200 centimeters of water would be considered a high arterial blood pressure.

In the above description, a specific example has been used to describe the injection site herein. However, it is understood by those skilled in the art that certain modifications can be made to this example without departing from the spirit and scope of the invention.

We claim:

1. A self-sealing subcutaneous injection site comprising:

a housing having a bottom wall and a resilient, generally dome-shaped wall defining an interior chamber, which interior chamber has a convex upper wall formed by a portion of the dome-shaped wall for providing compressive forces within such upper wall for sealing punctures through the upper wall upon fluid pressurization of such interior chamber; and a conduit extending through the dome-shaped wall into the interior chamber for providing a fluid-flow passageway to the interior chamber.

2. A self-sealing subcutaneous injection site as recited in claim 1 wherein the sidewall is constructed of a non-elongating resilient material.

3. A self-sealing subcutaneous injection site as recited in claim 1 wherein the interior chamber further comprises a convex-shaped chamber sidewall formed by a portion of the dome-shaped wall for providing compressive forces within the chamber sidewall for sealing punctures extending therethrough upon fluid pressurization of such chamber.

4. A self-sealing subcutaneous injection site as recited in claim 1 wherein the housing includes a generally flat upper, outer surface.

5. A self-sealing subcutaneous injection site as recited in claim 1 wherein the resilient dome-shaped wall comprises silicone elastomer.

6. A self-sealing subcutaneous injection site as recited in claim 1 wherein the housing is constructed of a silicone elastomer.

7. A self-sealing subcutaneous injection site as recited in claim 1 further comprising a needle guard extending along the bottom wall of the housing and at least partially positioned in the inner chamber.

8. A self-sealing subcutaneous injection site as recited in claim 1 wherein the bottom wall of the housing is constructed of a material impenetrable by a needle.

9. A self-sealing subcutaneous injection site as recited in claim 1 further comprising reinforcing cuff means extending around and imbedded in the resilient dome-shaped wall for reducing hoop strain in the resilient dome-shaped wall.

10. A self-sealing subcutaneous injection site as recited in claim 1 wherein the reinforcing cuff means comprises a Dacron mesh cuff.

11. A self-sealing subcutaneous injection site as recited in claim 1 further comprising a peripherally extending flange portion on the housing, which flange portion includes means for securing the housing within and to a patient.

* * * * *

UNITED STATES PATENT AND TRADEMARK OFFICE
CERTIFICATE OF CORRECTION

PATENT NO. : 4,543,088
DATED : September 24, 1985
INVENTOR(S) : Matthew W. Bootman and Ronald K. Yamamoto It is certified that error appears in the above-identified patent and that said Letters Patent are hereby corrected as shown below:

Column 6, line 64, after "herein" insert -- was --.

Column 8, line 57, change " $\leqq$ " to -- $\leq$ --.

Column 10, line 23, change "1" to -- 9 --.

Signed and Sealed this

Seventeenth Day of December 1985

[SEAL]

Attest:

DONALD J. QUIGG

Attesting Officer

Commissioner of Patents and Trademarks